(12) United States Patent
Lebon et al.

(10) Patent No.: US 6,613,361 B1
(45) Date of Patent: Sep. 2, 2003

(54) KETOPROFEN MICROGRANULES, METHOD FOR PREPARING SAME AND PHARMACEUTICAL COMPOSITIONS

(75) Inventors: Christophe Lebon, Rouvres (FR); Dominique Marechal, Dreux (FR); Pascal Suplie, Montaure (FR)

(73) Assignee: Laboratoires des Produits Ethiques Ethypharm, Houdan (FR)

( * ) Notice: Subject to any disclaimer, the term of this patent is extended or adjusted under 35 U.S.C. 154(b) by 0 days.

(21) Appl. No.: 09/959,265

(22) PCT Filed: Apr. 21, 2000

(86) PCT No.: PCT/FR00/01066

§ 371 (c)(1),
(2), (4) Date: Nov. 15, 2001

(87) PCT Pub. No.: WO00/64432

PCT Pub. Date: Nov. 2, 2000

(30) Foreign Application Priority Data

Apr. 22, 1999 (FR) .............................................. 90 05103

(51) Int. Cl.$^7$ ................................................ A61K 9/16
(52) U.S. Cl. ...................... 424/497; 424/456; 424/490; 424/497; 514/887
(58) Field of Search ................................. 424/441, 273, 424/497, 490, 456; 514/887

(56) References Cited

U.S. PATENT DOCUMENTS

| 4,447,443 A | * | 5/1984 | Goldenberg | ................. 424/273 |
| 4,871,396 A | * | 10/1989 | Tsujita et al. | ............. 106/286.8 |
| 4,980,170 A | | 12/1990 | Schneider Gerhard et al. | |
| 5,837,277 A | * | 11/1998 | Hayward | .................... 424/441 |

OTHER PUBLICATIONS

M. Dittgen et al., "Influence of the Pellet Coating on the Drug Release from Ketoprofen Slow Release Capsule," *Proceedings World Meeting on Pharmaceutics, Biopharmaceutics and Pharmaceutical Technology,* vol. 1, (1995), pp. 385–386.

I. Husson et al., "Modelling of Drug Release From Pellets Coated with an Insoluble Polymeric Membrane," *Journal of Controlled Release,* NL, Elsevier Science Publishers B.V. Amsterdam, vol. 17, No. 2, pp. 163–173.

* cited by examiner

Primary Examiner—Thurman K. Page
Assistant Examiner—Micah-Paul Young
(74) Attorney, Agent, or Firm—Foley & Lardner (57) ABSTRACT

The invention concerns ketoprofen microgranules with prolonged release each consisting of an active core containing ketoprofen coated with a polymeric film enabling prolonged release of the active principle and containing acrylic polymer coatings in a volume proportion substantially equal to 90/10.

21 Claims, 4 Drawing Sheets

KETOPROFEN MICROGRANULES, METHOD FOR PREPARING SAME AND PHARMACEUTICAL COMPOSITIONS

The present invention relates to a novel sustained-release pharmaceutical formulation of ketoprofen for daily oral administration, in the form of microgranules.

It also extends to the method for the preparation thereof and to the pharmaceutical compositions containing them.

Ketoprofen, or 2-(3-benzoylphenyl)propionic acid has been known since 1972 as a nonsteroidal anti-inflammatory medicinal product. It is commonly used for its analgesic, antipyretic and anti-inflammatory properties.

Ketoprofen is generally administered for the long-term symptomatic treatment of chronic inflammatory rheumatic diseases and of certain forms of osteoarthritis, and also for the short-term symptomatic treatment of acute triggering of abarticular rheumatism, microcrystalline arthritis, osteoarthritis, lumbago and severe radiculalgia.

The usual dose varies from 50 to 300 mg, preferably 100 to 200 mg, per day, in one or more doses.

Given that ketoprofen is commonly used in long-term treatments, and that its half-life is short (approximately 2 hours), sustained-release forms need to be used.

Document EP-A-403 383 describes sustained-release granules which each comprise a core comprising ketoprofen and microcrystalline cellulose and a coating comprising a water-soluble cellulose derivative and a water-insoluble cellulose derivative. The mass proportion of ketoprofen is between 60 and 80%; it is preferably equal to 75%. The granule cores are obtained by extrusion/spheronization and the coating thereof is carried out in a fluidized air bed using a solution of the two cellulose derivatives in a MeOH/$CH_2Cl_2$ mixture.

The granules described in EP-A-403 383, for example the specialty product Profenid® LP 200 mg, have the disadvantage of being obtained using a method which uses organic solvents.

Document EP-A-361 910 describes one of the dispersible granules prepared by adsorbing a pulverulent active principle having a granule size of less than 100 microns, on to a pulverulent excipient having a granule size of between 250 and 500 microns. The active principle may be ketoprofen and the excipient may be lactose. The particles obtained are mixed with an excipient which is solid at room temperature and which has a low melting point, for example stearic acid or a polyethylene glycol derivative. The mixture is heated until this excipient melts, and cooled in order to resolidify this same excipient once it has become attached to the particles of active principle.

The granules described in EP-A-361 910 contain active principle contents of the order of 25%, and appear to be restricted to these low contents.

Document EP-A-204 596 describes sustained-release ketoprofen granules obtained by extrusion of a mixture of ketoprofen, of one or more erodible polymers and of at least two lipid excipients, one of which has the property of gelling the polymer(s) and the other has lubricating properties. The polymer is, for example,. ethylcellulose, an acrylate or a vinylpyrrolidone/vinyl acetate copolymer. The lipid excipients are fatty acids or plant oils.

The granules described in EP-A-204 596 unadvantageously have release profiles which are extremely variable from one formulation to the other.

Document EP-A-667 148 describes delayed-release ketoprofen tablets consisting of a core of active principle coated with a cationic polymer and then with an anionic polymer. The cationic polymer is soluble at a pH of less than or equal to 6, for example an aminoalkyl methacrylate copolymer. The anionic polymer is soluble at a pH of greater than or equal to 5.5. The anionic polymer may be chosen from a methacrylic acid/methacrylate L copolymer (Eudragit L®), a methacrylic acid/methacrylate S copolymer (Eudragit S®) and hydroxypropylmethylcellulose.

The study of the bioavailability of this formulation (FIG. 2 of document EP-A-667 148) shows that the plasma concentration of ketoprofen is virtually zero for the 13 hours following administration of the tablet containing 50 mg of ketoprofen, and then increases in linear fashion up to 1.5 $\mu$g/ml during the next 3 hours.

The specialty product ORUVAIL® 200 mg is manufactured using granules consisting of sucrose and starch, encoated with shellac and ethylcellulose. However, products containing shellac pose problems of stability. In addition, the preparation of a formulation containing shellac and ethylcellulose requires the use of an organic solvent.

The object of the present invention is to provide an oral sustained-release formulation of ketoprofen which lacks the drawbacks of the prior art, i.e.

the preparation of which uses no organic solvent, and
the excipients of which are chemically compatible so as to confer on the formulation good stability over time.

For this reason, the present invention relates to sustained-release ketoprofen microgranules, each consisting of an active core containing ketoprofen coated with a polymeric layer which allows sustained release of the active principle, characterized in that the polymeric layer contains Eudragit® RL and Eudragit® RS in a mass proportion of between 80/20 and 95/5, preferably approximately equal to 90/10.

Eudragit® RL and Eudragit® RS are aqueous dispersions at 30% of the copolymer poly(ethyl acrylate, methyl methacrylate, trimethylammonioethyl methacrylate chloride) in the proportions 1/2/0.2 and 1/2/0.1, respectively.

The combination of Eudragit® RL and Eudragit® RS according to the invention has many advantages.

Eudragit® RL and Eudragit® RS are water-miscible in any proportion and do not require the use of organic solvents.

The film obtained using Eudragit® RL and Eudragit® RS is insoluble in water and in digestive fluids, to such an extent that the active principle is released by diffusion; in addition, the permeability of this film is independent of the pH, such that the release of the active principle is independent of the local and individual variations of the digestive tract.

The properties of the film containing Eudragit® RL and Eudragit® RS are perfectly suitable for coating granules.

The total mass of Eudragit® RL and Eudragit® RS contained in the polymeric layer represents between 1 and 8% of the mass of the microgranule, preferably 2 and 5%.

Advantageously, the polymeric layer coating the core contains a plasticizer, such as triethyl citrate, and/or a lubricant, chosen from pharmaceutically acceptable lubricants, such as colloidal anhydrous silica or Syloid®.

The plasticizer enhances the elasticity of the polymeric film and decreases the temperature at which the film forms. The plasticizer represents 10 to 20% by weight of the dry mass of Eudragit® RL and RS.

The lubricant represents 10 to 30% by weight of the dry mass of Eudragit® RL and RS.

The mass of ketoprofen contained in the active core represents 50 to 80% of the mass of the microgranule, preferably 65 to 75%, more preferably 70% approximately.

The active core advantageously consists of a neutral support grain coated with ketoprofen and with a binding agent, chosen from pharmaceutically acceptable binding agents, for example a polyacrylate. In this embodiment, the neutral support grain represents 10 to 40% by weight of the mass of the microgranule, preferably 20 to 25%.

The active core of the microgranules of the invention preferably contains Eudragit® NE 30 D as a binding agent.

Eudragit® NE is an aqueous dispersion at 30% of an acrylic copolymer: poly(ethyl acrylate, methyl methacrylate) in the proportions 2/1.

Eudragit® NE has the advantage of being chemically compatible with the Eudragit® RL and RS contained in the enteric layer. It forms a film which is insoluble in water and in the digestive fluids.

A subject of the present invention is also a method for preparing the sustained-release ketoprofen microgranules presented above.

The method according to the invention is characterized in that it comprises a step for coating the active core by spraying an aqueous suspension containing Eudragit® RS and Eudragit® RL.

The active core is advantageously obtained by assembling the ketoprofen on neutral support grains with an aqueous suspension of a binding agent such as a polyacrylate.

According to a preferred embodiment, a first step of the method consists in preparing an "assembly" suspension consisting of a 30% by weight aqueous suspension of Eudragit® NE 30D®.

The assembly of the ketoprofen is carried out in a sugar-coating pan on neutral support grains, by discontinuous spraying of the suspension described above, alternating with sequences of dusting of the ketoprofen.

The microgranules are then sieved and dried at approximately 60° C. for at least 10 hours.

A second step consists in preparing a coating suspension consisting of a 50% by weight aqueous solution of a mixture of Eudragit RL®, Eudragit RS®, silica and triethyl citrate in mass proportions of between 8/2/2/2 and 9.5/0.5/2/2, preferably equal to 9/1/2/2.

The microgranules to be coated are then placed in a sugar-coating pan and sprayed continuously with the coating suspension described above.

The coated microgranules are then sieved and dried at approximately 40° C. for 4 to 8 hours.

The coating may be carried out in several steps, depending on the desired kinetics.

The dried microgranules may optionally be lubricated with talc, and then placed in gelatin capsules or tablets, containing 50 to 300 mg, preferably 100 mg to 200 mg, of ketoprofen.

The present invention also relates to any pharmaceutical composition which contains the microgranules which are described above and which can be obtained using the method which has just been presented, the mass of the microgranules contained in said composition corresponding to a daily dose of 50 to 300 mg, preferably 100 to 200 mg, approximately, of ketoprofen.

The in vivo dissolution profile of the microgranules and of the gelatin capsules according to the invention is such that
  15 to 35% of the active principle, preferably 20 to 30%, has been released after two hours,
  45 to 70% of the active principle, preferably 50 to 65%, has been released after 6 hours,
  more than 65% of the active principle, preferably 70%, or even 80%, has been released after 12 hours.

The following examples illustrate the invention without limiting the scope thereof.

EXAMPLE 1

Microgranules YXK 002 A; Gelatin Capsules 8308 a) Preparation of the Microgranules

Microgranules having the following composition are prepared using the method described hereinafter,

TABLE 1

Composition of the microgranules of example 1

|  | AMOUNT IN % MASS |
|---|---|
| Ketoprofen | 70.02% |
| Neutral grains | 23.11% |
| Eurdragit NE 30 D ® | 3.54% |
| Eudragit RS 30 D ® | 1.83% |
| Eudragit RL 30 D ® | 0.21% |
| CITROFLEX ® (triethyl citrate) | 0.40% |
| AEROSIL 200 ® (silica) | 0.40% |
| Talc | 0.49% |
| Content of ketoprofen | 713 mg/g |

Preparation of the Assembly Suspension

The suspension is prepared in a stainless steel container. Purified water is poured into the container and then stirred. 15% by weight of Eudragit NE 30D® is slowly added to the water after vigorous agitation of the flask containing it.

The stirring is maintained until the suspension is homogeneous.

Assembly of ketoprofen on the Neutral Support Grains

Neutres 30® support grains are placed in a rotating sugar-coating pan.

The active principle is assembled on the Neutres 30® by discontinuous spraying of the assembly suspension containing the binding agent, alternating with sequences of dusting of the ketoprofen and pause sequences.

The mass of microgranules obtained is sieved over a grid with a mesh size ranging from 0.355 to 1.25 mm. The microgranules are then dried in the rotating pan at 60° C., this being for 10 hours.

Preparation of the Coating Suspension

A 15% aqueous suspension containing the following excipients is prepared:

| EUDRAGIT RL 30D ® | 90.0% of the total mass of the Eudragit dry extract |
| EUDRAGIT RS 30D ® | 10.0% of the total mass of the Eudragit dry extract |
| SILICA | 20.0% of the total mass of the Eudragit dry extract |
| TRIETHYL CITRATE | 20.0% of the total mass of the Eudragit dry extract |

The suspension is prepared in a stainless steel container into which purified water is introduced, followed by the Eudragit RS® after vigorous stirrion of the flask containing it. The stirrion is maintained until the suspension is homogeneous. The Eudragit RL® is then incorporated after vigorous stirrion of the flask containing it.

The silica and then the triethyl citrate are incorporated little by little into the suspension. The stirrion is maintained until the mixture is homogeneous, and then throughout the coating.

Coating of the Ketoprofen Microgranules

The microgranules to be coated are placed in a sugar-coating pan. The microgranules are coated by continuous spraying of the suspension described above.

The mass of microgranules obtained is sieved over a grid with a mesh size of between 0.355 and 1.25 mm.

The microgranules are then dried in a rotating pan at a temperature of 35° C. for 7 hours.

The coating step is carried out according to this protocol, in one or more successive phases if necessary, in order to obtain the desired kinetics.

The microgranules are lubricated with talc for one minute.

The content of ketoprofen is determined by dissolving the microgranules in a methanol/water mixture (3/1 by volume) and then measuring UV absorbence at 257 nm.

b) In Vitro Dissolution Profile of the Microgranules

The in vitro dissolution profile of the microgranules obtained above is established according to the following protocol:

The amount of microgranules, as obtained above, corresponding to 200 mg of ketoprofen is dissolved in 900 ml of water at pH=6.9, at 37° C., with stirrion at 75 rpm, for 24 hours, in a vane machine described in the 3rd edition of the European pharmacopoeia.

The concentration of ketoprofen is measured by UV spectrophotometry at 260 nm.

The results are given in table 2 below.

TABLE 2

In vitro dissolution of the microgranules of example 1

| TIME (hour) | Percentage of dissolved ketoprofen |
|---|---|
| 1 hour | 19.7% |
| 2 hours | 34.8% |
| 3 hours | 46.6% |
| 4 hours | 55.2% |
| 5 hours | 61.7% |
| 6 hours | 66.6% |
| 7 hours | 70.5% |
| 8 hours | 73.7% | c) In Vitro Dissolution Profile of 200-mg Gelatin Capsules

The mass of microgranules required to obtain the equivalent of 200 mg of ketoprofen is calculated and then placed in a size 1 gelatin capsule. The dissolution profile of the gelatin capsules is produced under the same conditions as for the microgranules.

The results are given in the table below.

TABLE 3

In vitro dissolution of the 200-mg gelatin capsules containing the microgranules of example 1

| TIME (hour) | Percentage of dissolved ketoprofen |
|---|---|
| 1 hour | 17.5% |
| 2 hours | 31.7% |
| 3 hours | 43.2% |
| 4 hours | 52.0% |
| 5 hours | 58.7% |
| 6 hours | 63.9% |
| 7 hours | 68.1% |
| 8 hours | 71.6% |
| 9 hours | 74.6% |
| 10 hours | 77.2% |
| 11 hours | 79.5% |
| 12 hours | 81.3% | d) In Vivo Dissolution of the 200-mg Gelatin Capsules

A randomized, double blind, two-way crossover in vivo study is carried out on 5 individuals to which a single gelatin capsule containing 200 mg of ketoprofen is administered.

Figure 1:
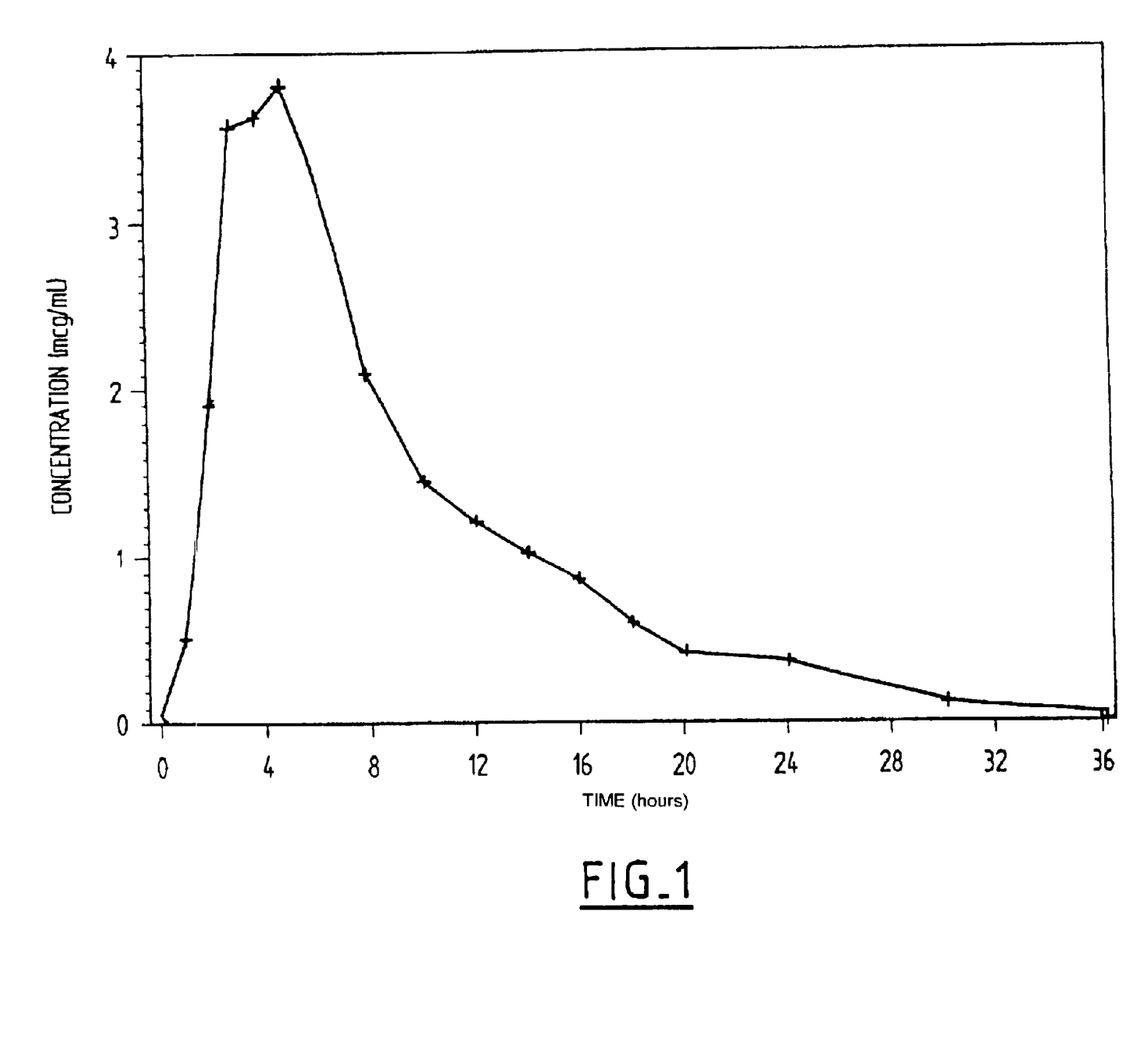
FIGS. 1 to 3 give the results of in vivo dissolution of the gelatin capsules of examples 1 to 3, respectively. The curve represents the evolution over time of the mean plasma concentration of ketoprofen, measured in five patients, after administration to each one of them of a size 1 gelatin capsule containing an amount of microgranules of example 1 corresponding to 200 mg of ketoprofen.

Table 4 and FIG. 1 summarize the results obtained.

TABLE 4

In vivo kinetic parameters for the 200-mg gelatin capsules containing the microgranules of example 1

| Parameter | Mean |
|---|---|
| $AUC_{0-t}$ ($\mu g \cdot h \cdot ml^{-1}$) | 35.8 |
| $AUC_{inf}$ ($\mu g \cdot h \cdot ml^{-1}$) | 39.0 |
| $C_{max}$ ($\mu g \cdot ml^{-1}$) | 4.4 |
| $T_{max}$ (h) | 3.5 |
| $T_{1/2}$ (h) | 7.7 | e) Study of Stability of 100-mg Gelatin Capsules

The stability of the 100-mg gelatin capsules packaged in PCV/alu blister packs placed in normal storage conditions (25° C., 60% relative humidity) are studied for 28 months.

The results of this study are summarized in table 5.

TABLE 5

Assays for stability of the 100-mg gelatin capsules containing microgranules of example 1

| | | STANDARDS | TIME 0 | 21 months | 28 months |
|---|---|---|---|---|---|
| 1. | Description | Gelatin capsules containing off-white spherical microgranules | Standard | Standard | Standard |
| 2. | Principle weight | 129.25 to 157.95 mg/ gelatin capsule | 140.5 mg | 140.8 mg | 140.4 mg |

TABLE 5-continued

Assays for stability of the 100-mg gelatin capsules containing microgranules of example 1

| | | STANDARDS | TIME 0 | 21 months | 28 months |
|---|---|---|---|---|---|
| 3. | Test for impurities | | | | |
| | 3-acetyl-benzophenone | ≦0.2% | — | — | — |
| | Total of other impurities | ≦0.6% | — | — | 0.08% |
| 4. | Content of ketoprofen | 95.0 to 105.0 mg/ gelatin capsule | 98.0 mg | 99.4 mg | 99.8 mg |
| 5. | Dissolution of test: | | | | |
| | after 2 hours | 15–35% | 32.2% | 33.6% | 32.5% |
| | after 6 hours | 45–70% | 63.6% | 65.6% | 63.9% |
| | after 8 hours | ≧65% | 71.2% | 72.7% | 71.2% |

EXAMPLE 2

Microgranules YXK 002 A1; Gelatin Capsules 8494 a) Preparation of the Microgranules

The microgranules having the following composition are prepared according to the method described in example 1:

TABLE 6

Composition of the microgranules of example 2

| | AMOUNT IN % MASS |
|---|---|
| Ketoprofen | 69.46% |
| Neutral grains | 22.94% |
| Eurdragit NE ® 30 D | 3.53% |
| Eudragit RS ® 30 D | 2.01% |
| Eudragit RL ® 30 D | 0.23% |
| CITROFLEX ® (triethyl citrate) | 0.43% |
| AEROSIL ® 200 (silica) | 0.43% |
| Talc | 0.97% |
| Content of ketoprofen | 709 mg/g | b) In Vitro Dissolution Profile of the Microgranules

The in vitro dissolution profile of the microgranules, obtained under the same conditions as example 1, is given in table 7.

TABLE 7

In vitro dissolution of the microgranules of example 2

| TIME (hour) | Percentage of dissolved ketoprofen |
|---|---|
| 1 hour | 13.1% |
| 2 hours | 24.1% |
| 3 hours | 33.5% |
| 4 hours | 41.2% |
| 5 hours | 47.6% |
| 6 hours | 52.9% |
| 7 hours | 57.3% |
| 8 hours | % | a) In Vitro Dissolution Profile of the 200-mg Gelatin Capsules:

The in vitro dissolution profile of the gelatin capsules containing an amount of the microgranules obtained above which corresponds to 200 mg of ketoprofen is determined under the conditions of example 1.

The results are given in table 8.

TABLE 8

In vitro dissolution of the 200-mg gelatin capsules containing the microgranules of example 2

| TIME (hour) | Percentage of dissolved ketoprofen |
|---|---|
| 1 hour | 14.3% |
| 2 hours | 26.5% |
| 3 hours | 36.8% |
| 4 hours | 45.2% |
| 5 hours | 51.9% |
| 6 hours | 57.2% |
| 7 hours | 61.5% |
| 8 hours | 65.1% |
| 9 hours | 68.3% |
| 10 hours | 71.1% |
| 11 hours | 73.5% |
| 12 hours | 75.5% | d) In Vivo Dissolution Profile of the 200-mg Gelatin Capsules

A randomized, "three-way cross over?" in vivo study is carried out on 5 individuals to which a single gelatin capsule containing 200 mg of ketoprofen is administered.

Figure 2:
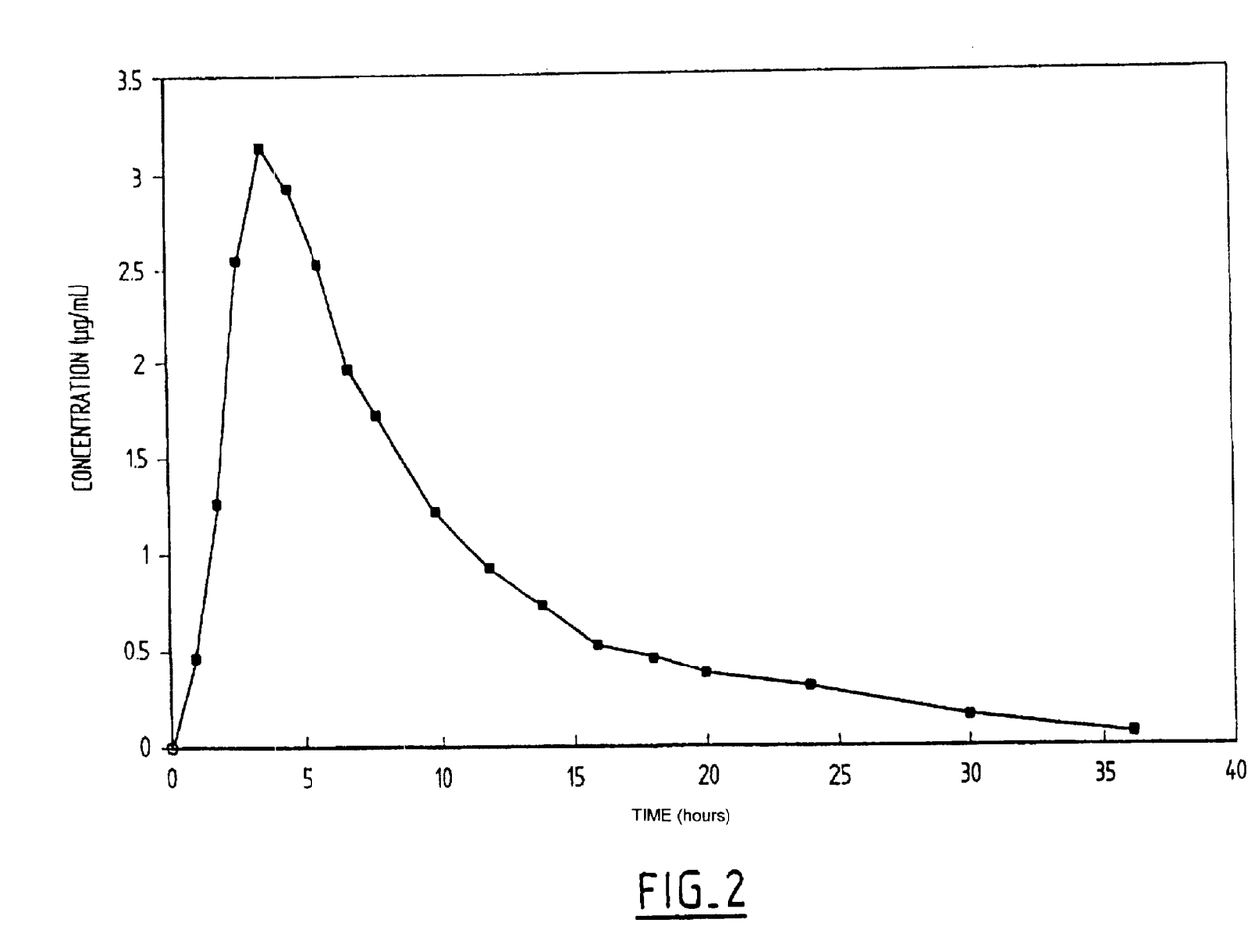

Table 9 and FIG. 2 summarize the results obtained.

TABLE 9

In vivo kinetic parameters for the 200-mg gelatin capsules containing the microgranules of example 2

| Parameter | Mean |
|---|---|
| $AUC_{0-t}$ ($\mu g \cdot h \cdot ml$) | 27.87 |
| $AUC_{inf}$ ($\mu g \cdot h \cdot ml$) | 31.88 |
| $C_{max}$ ($\mu g \cdot ml$) | 3.16 |

EXAMPLE 3

Microgranules YKET 003; Gelatin Capsules 8500 a) Preparation of the Microgranules:

The microgranules having the following composition are prepared according to the method described in example 1:

TABLE 10

Composition of the microgranules of example 3

| | AMOUNT IN % MASS |
|---|---|
| Ketoprofen | 68.73% |
| Neutral grains | 22.69% |
| Eurdragit NE ® 30 D | 3.48% |
| Eudragit RS ® 30 D | 2.34% |
| Eudragit RL ® 30 D | 0.27% |
| CITROFLEX ® (triethyl citrate) | 0.51% |
| AEROSIL ® 200 (silica) | 0.51% |
| Talc | 1.47% |
| Content of ketoprofen | 695 mg/g | b) In Vitro Dissolution Profile of the Microgranules:

The in vitro dissolution profile of the microgranules and of the gelatin capsules, obtained under the same conditions as example 1, is given in table 11.

TABLE 11

In vitro dissolution of the microgranules of example 3

| TIME (hour) | Percentage of dissolved ketoprofen |
|---|---|
| 1 hour | 12.1% |
| 2 hours | 22.7% |
| 3 hours | 32.1% |
| 4 hours | 40.3% |
| 5 hours | 47.4% |
| 6 hours | 53.3% |
| 7 hours | 58.1% |
| 8 hours | 62.2% |
| 9 hours | 65.7% |
| 10 hours | 68.8% |
| 11 hours | 71.5% |
| 12 hours | 74.0% | c) In Vitro Dissolution Profile of the 200-mg Gelatin Capsules

The in vitro dissolution profile of the gelatin capsules containing an amount of the microgranules obtained above which corresponds to 200 mg of ketoprofen is determined under the conditions of example 1.

The results are given in table 12.

TABLE 12

In vitro dissolution of the 200-mg gelatin capsules containing the microgranules of example 3

| TIME (hour) | Percentage of dissolved ketoprofen |
|---|---|
| 1 hour | 11.3% |
| 2 hours | 21.2% |
| 3 hours | 29.9% |
| 4 hours | 37.8% |
| 5 hours | 44.4% |
| 6 hours | 49.9% |
| 7 hours | 54.7% |
| 8 hours | 58.7% |
| 9 hours | 62.2% |
| 10 hours | 65.3% |
| 11 hours | 67.9% |
| 12 hours | 70.3% | d) In Vivo Dissolution Profile of the 200-mg Gelatin Capsules

A randomized, three-way crossover, in vivo study is carried out on 5 individuals to which a single gelatin capsule containing 200 mg of ketoprofen is administered.

Figure 3:
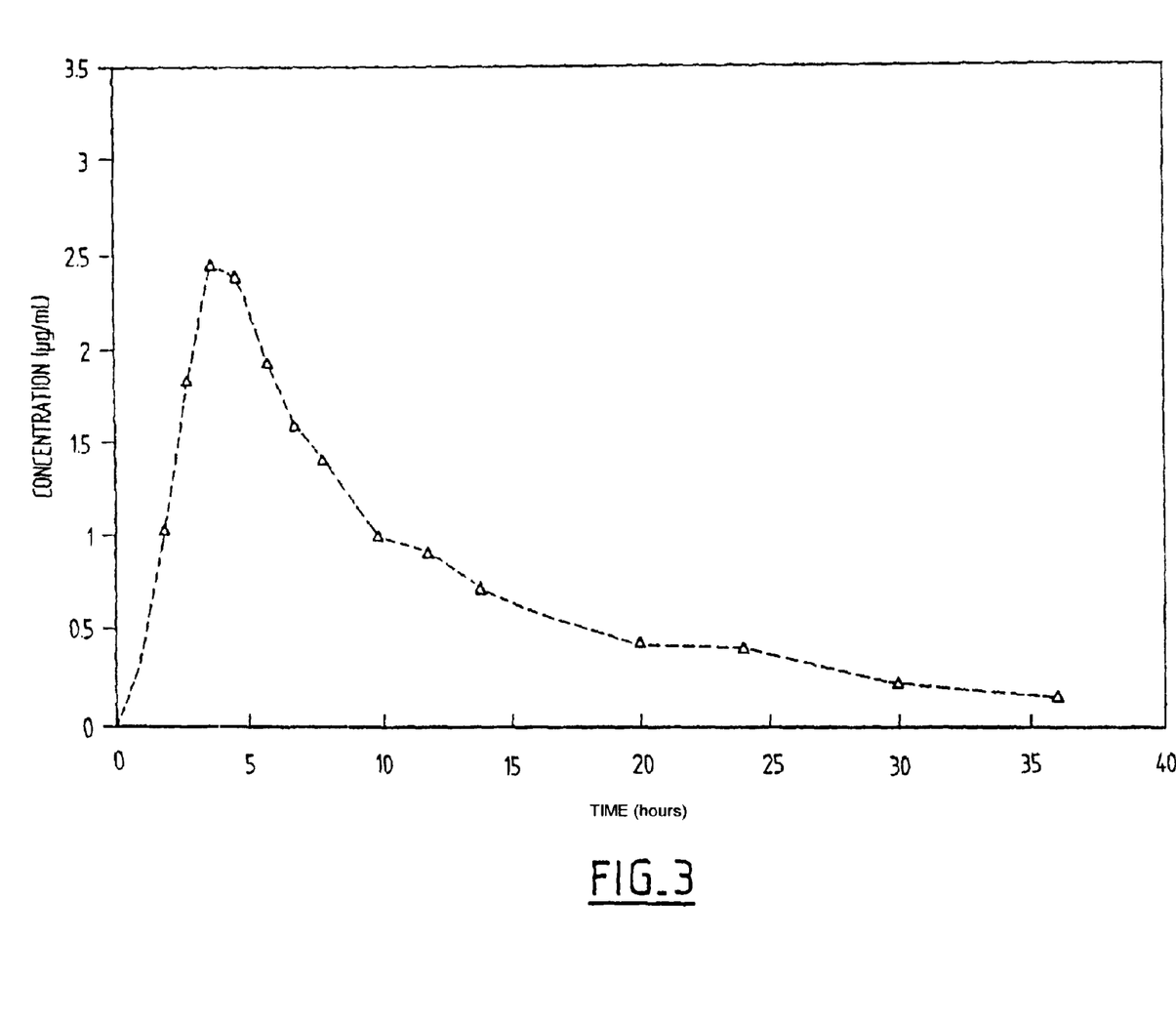

Table 13 and FIG. 3 summarizes the results obtained.

TABLE 13

In vivo kinetic parameters for the 200-mg gelatin capsules containing the microgranules of example 3

| Parameter | Mean |
|---|---|
| $AUC_{0-t}$ ($\mu g \cdot h \cdot ml^{-1}$) | 25.75 |
| $AUC_{inf}$ ($\mu g \cdot h \cdot ml^{-1}$) | 30.39 |
| $C_{max}$ ($\mu g \cdot ml^{-1}$) | 2.47 |

EXAMPLE 4

Microgranules YKET 006; Gelatin Capsules 8571 a) Preparation of the Microgranules

The microgranules having the following composition are prepared according to the method described in example 1.

TABLE 14

Composition of the microgranules of example 4

| | AMOUNT IN % MASS |
|---|---|
| Ketoprofen | 68.94% |
| Neutral grains | 22.75% |
| Eurdragit NE ® 30 D | 3.49% |
| Eudragit RS ® 30 D | 2.16% |
| Eudragit RL ® 30 D | 0.25% |
| CITROFLEX ® (triethyl citrate) | 0.47% |
| AEROSIL 200 ® (silica) | 0.47% |
| Talc | 1.47% |
| Content of ketoprofen | 706 mg/g | b) In Vitro Dissolution Profile of the Microgranules and of the Gelatin Capsules:

The in vitro dissolution profile of the microgranules and of the gelatin capsules, obtained under the same conditions as example 1, is given in table 15.

TABLE 15

In vitro dissolution of the microgranules of example 4

| TIME (hour) | Percentage of dissolved ketoprofen |
|---|---|
| 1 hour | 12.9% |
| 2 hours | 24.3% |
| 3 hours | 34.2% |
| 4 hours | 42.7% |
| 5 hours | 49.7% |
| 6 hours | 55.6% |
| 7 hours | 60.4% |
| 8 hours | 64.5% |
| 9 hours | 67.9% |
| 10 hours | 70.9% |
| 11 hours | 73.4% |
| 12 hours | 75.7% | c) In Vitro Dissolution Profile of the 200-mg Gelatin Capsules:

The in vitro dissolution profile of the gelatin capsules containing an amount of the microgranules obtained above which corresponds to 200 mg of ketoprofen is determined under the conditions of example 1.

The results are given in table 16.

TABLE 16

In vitro dissolution of the 20-mg gelatin capsules containing the microgranules of example 4

| TIME (hour) | Percentage of dissolved ketoprofen |
|---|---|
| Dissolution test | |
| 1 hour | 11.9% |
| 2 hours | 22.1% |
| 3 hours | 31.2% |
| 4 hours | 39.2% |
| 5 hours | 46.1% |
| 6 hours | 51.8% |
| 7 hours | 56.8% |
| 8 hours | 61.1% |
| 9 hours | 64.5% |
| 10 hours | 68.0% |
| 11 hours | 70.8% |
| 12 hours | 73.3% | d) In Vivo Dissolution Profile of the 20-mg Gelatin Capsules

A randomized, two-way crossover, in vivo study is carried out on 20 individuals to which a single gelatin capsule containing 20 mg of ketoprofen is administered.

Figure 4:
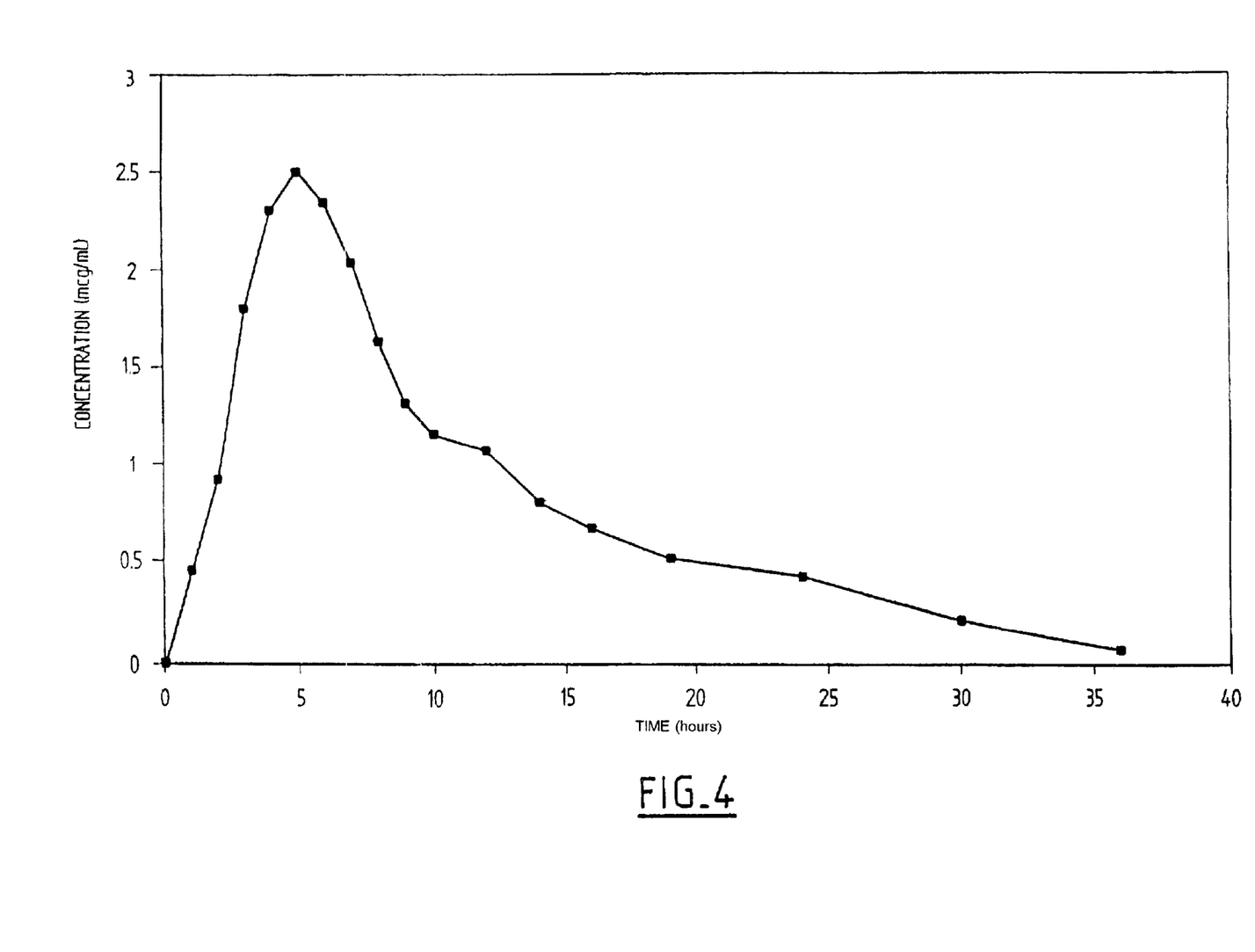
FIG. 4 gives the results of in vivo dissolution of gelatin capsules of example 4. The curve represents the evolution over time of the plasma concentration measured in 20 patients, after administration to each one of them of a size 1 gelatin capsule containing an amount of microgranules of example 4 corresponding to 200 mg of ketoprofen.

Table 17 and FIG. 4 summarize the results obtained.

TABLE 17

In vivo kinetic parameters of the 200-mg gelatin capsules containing the microgranules of example 4

| Parameter | Mean |
|---|---|
| $AUC_{0-t}$ ($\mu g \cdot h \cdot ml^{-1}$) | 28.01 |
| $AUC_{inf}$ ($\mu g \cdot h \cdot ml^{-1}$) | 29.94 |
| $C_{max}$ ($\mu g \cdot ml^{-1}$) | 2.92 | e) Study of Stability of the 200-mg Gelatin Capsules

The stability of the 200-mg gelatin capsules packaged in PVC/Alu blister packs is studied for 16 months under normal storage conditions (21° C., 60% relative humidity). The results are given in the table below.

What is claimed is:

1. A sustained-release ketoprofen microgranule consisting of an active core containing ketoprofen coated with a polymeric layer which allows sustained release of the active principle, wherein the polymeric layer contains a 30% aqueous dispersion of the copolymer poly(ethyl acrylate, methyl methacrylate, trimethylammonioethyl methacrylate chloride) in the proportion 1/2/0.2 and a 30% aqueous dispersion of the copolymer poly(ethyl acrylate, methyl methacrylate, trimethylammonioethyl methacrylate chloride) in the proportion 1/2/0.1, in a mass proportion of between 80/20 and 95/5.

2. The microgranule as claimed in claim 1, wherein the total mass of 30% aqueous dispersion of copolymer poly (ethyl acrylate, methyl methacrylate, trimethylammonioethyl methacrylate chloride) in the proportion 1/2/0.2 and of 30% aqueous dispersion of the copolymer poly(ethyl acrylate, methyl methacrylate, trimethylammonioethyl methacrylate chloride) in the proportion 1/2/0.1, represents between 1 and 8% of the mass of the microgranule.

3. The microgranule as claimed in claim 1, wherein the enteric layer coating the core contains a plasticizer.

4. The microgranule as claimed in claim 1, wherein the ketoprofen represents 50 to 80% by weight of the microgranule.

5. The microgranule as claimed in claim 1, wherein the core consists of a neutral support grain coated with ketoprofen and with a binding agent.

6. The microgranule as claimed in claim 5, wherein the neutral support grain represents 10 to 40% by weight of the mass of the microgranule.

7. A method for preparing the microgranules of claim 1 comprising a step for coating the active core by spraying an aqueous solution containing a 30% aqueous dispersion of the copolymer poly(ethyl acrylate, methyl methacrylate, trimethylammonioethyl methacrylate chloride) in the proportion 1/2/0.2 and a 30% aqueous dispersion of the copolymer poly(ethyl acrylate, methyl methacrylate, trimethylammonioethyl methacrylate chloride) in the proportion 1/2/0.1.

8. The method as claimed in claim 7, wherein the active core is obtained by assembling the ketoprofen on neutral support grains with an aqueous suspension of a binding agent.

9. A pharmaceutical composition containing a mass of microgranules consisting of an active core containing keto-

| | | STANDARDS | TIME 0 | 3 MONTHS | 6 MONTHS | 12 MONTHS |
|---|---|---|---|---|---|---|
| 1. | Description | Gelatin capsules containing off-white spherical microgranules | Standard | Standard | Standard | Standard |
| 2. | Principle weight | 258.5 to 315.9 mg/ gelatin capsule | 284.7 mg | 283.3 mg | 284.1 mg | 283.2 mg |
| 3. | Test for impurities | | | | | |
| | 3-acetylbenzophenone | ≦0.2% | — | — | — | — |
| | total of other impurities | ≦0.6% | — | — | — | — |
| 4. | Content of ketoprofen | 190.0 to 210.0 mg/ gelatin capsule | 199.6 mg | 197.1 mg | 197.1 mg | 198.3 mg |
| 5. | Dissolution test | | | | | |
| | after 2 hours | 15–35% | 22.0% | 23.6% | 21.5% | 20.6% |
| | after 6 hours | 45–70% | 51.1% | 55.0% | 51.1% | 49.3% |
| | after 12 hours | ≧65% | 70.3% | 75.2% | 71.9% | 70.8% |
| | after 24 hours | ≧80% | 84.0% | 90.4% | 88.0% | 85.0% |
| 6. | Content of water | Not defined | 2.90% | 0.7% | 0.6% | 0.5% | profen coated with a polymeric layer which allows sustained release of the active principle, wherein the polymeric layer contains a 30% aqueous dispersion of the copolymer poly (ethyl acrylate, methyl methacrylate, trimethylammonioethyl methacrylate chloride) in the proportion 1/2/0.2 and a 30% aqueous dispersion of the copolymer poly(ethyl acrylate, methyl methacrylate, trimethylammonioethyl methacrylate chloride) in the proportion 1/2/0.1, in a mass proportion of between 80/20 and 95/5 or prepared according to the method of claim 8, which corresponds to a daily dose of 50 to 300 mg approximately of ketoprofen.

10. The microgranule as claimed in claim 1, wherein the mass proportion is approximately equal to 90/10.

11. The microgranule as claimed in claim 2, wherein the mass of the aqueous dispersions represent between 2 and 5% of the mass of the microgranule.

12. The microgranule as claimed in claim 3, wherein the enteric layer containing the core also contains a lubricant.

13. The microgranule as claimed in claim 12, wherein the lubricant is silica.

14. The microgranule as claimed in claim 1, wherein the enteric layer coating the core contains a lubricant.

15. The microgranule as claimed in claim 14, wherein the lubricant is silica.

16. The microgranule as claimed in claim 4, wherein the ketoprofen represents 65 to 75% by weight of the microgranule.

17. The microgranule as claimed in claim 5, wherein the binding agent is a polyacrylate.

18. The microgranule as claimed in claim 6, wherein the neutral support grain represents 20 to 25% by weight of the mass of the microgranule.

19. The microgranule as claimed in claim 8, wherein the binding agent is a polyacrylate.

20. The pharmaceutical composition as claimed in claim 9, wherein the daily dose of ketoprofen is 100 mg to 200 mg.

21. The microgranule as claimed in claim 3, wherein the plasticizer is triethyl citrate.

* * * * *

UNITED STATES PATENT AND TRADEMARK OFFICE
CERTIFICATE OF CORRECTION

PATENT NO. : 6,613,361 B1
DATED : September 2, 2003
INVENTOR(S) : Christophe Lebon, Dominique Marechal and Pascal Suplie It is certified that error appears in the above-identified patent and that said Letters Patent is hereby corrected as shown below:

Column 4,
Lines 28-29, "Eudragit RS 30 D" should read -- Eudragit RL 30 D --; and "Eudragit RL 30 D" should read -- Eudragit RS 30 D --.

Column 7,
Lines 35-36, "Eudragit RS 30 D" should read -- Eudragit RL 30 D --; and "Eudragit RL 30 D" should read -- Eudragit RS 30 D --; and Column 9,
Lines 9-10, "Eudragit RS 30 D" should read -- Eudragit RL 30 D --; and "Eudragit RL 30 D" should read -- Eudragit RS 30 D --.

Signed and Sealed this

Fourth Day of January, 2005

JON W. DUDAS
*Director of the United States Patent and Trademark Office*